(12) United States Patent
Osborne et al.

(10) Patent No.: US 10,449,319 B2
(45) Date of Patent: Oct. 22, 2019

(54) RESPIRATORY HUMIDIFICATION SYSTEM

(71) Applicant: FISHER & PAYKEL HEALTHCARE LIMITED, Auckland (NZ)

(72) Inventors: Hamish Adrian Osborne, Auckland (NZ); Jonathan David Harwood, Auckland (NZ); Natalie May Robertson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 522 days.

(21) Appl. No.: 15/115,751

(22) PCT Filed: Feb. 9, 2015

(86) PCT No.: PCT/NZ2015/050011
§ 371 (c)(1),
(2) Date: Aug. 1, 2016

(87) PCT Pub. No.: WO2015/119515
PCT Pub. Date: Aug. 13, 2015

(65) Prior Publication Data
US 2017/0173293 A1    Jun. 22, 2017

Related U.S. Application Data

(60) Provisional application No. 61/937,017, filed on Feb. 7, 2014.

(51) Int. Cl.
*A61M 16/08* (2006.01)
*A61M 16/10* (2006.01)
(Continued)

(52) U.S. Cl.
CPC .... *A61M 16/0808* (2013.01); *A61M 16/0816* (2013.01); *A61M 16/0875* (2013.01);
(Continued)

(58) Field of Classification Search
CPC .. A61M 16/00; A61M 16/0057; A61M 16/08; A61M 16/0808; A61M 16/0816;
(Continued)

(56) References Cited

U.S. PATENT DOCUMENTS 2,590,797 A * 3/1952 Siciliano ............... F16L 43/003
                                                    138/39
3,623,511 A * 11/1971 Levin ..................... F15D 1/04
                                                    138/177
(Continued)

FOREIGN PATENT DOCUMENTS

EP           2703034 A2 * 3/2014 ............ A61M 16/16
WO    WO 2009/127192 A1    10/2009

OTHER PUBLICATIONS

International Search Report; PCT/NZ2015/050011; dated Mar. 19, 2015; 3 pages.

*Primary Examiner* — Joseph D. Boecker
(74) *Attorney, Agent, or Firm* — Knobbe Martens Olson & Bear LLP

(57) ABSTRACT

A system provides warm, humidified gas to a patient via a patient interface. Horizontal connections can be used between the humidification chamber and conduit. To reduce the likelihood of condensate flowing back to the humidification chamber, or dead space or gases recirculation regions occurring within the gases flow path, a raised portion is positioned inside of the flow path to improve flow characteristics and to provide a barrier for condensate back flow. The raised portion also reduces the amount of condensate that is formed in the system and provides better flow characteristics for sensing purposes.

15 Claims, 18 Drawing Sheets

(51) Int. Cl.
*A61M 16/16* (2006.01)
*F15D 1/06* (2006.01)
*F24F 13/08* (2006.01)

(52) U.S. Cl.
CPC ...... *A61M 16/109* (2014.02); *A61M 16/1095* (2014.02); *A61M 16/16* (2013.01); *A61M 2205/3368* (2013.01); *A61M 2205/50* (2013.01); *F15D 1/06* (2013.01); *F24F 13/081* (2013.01)

(58) Field of Classification Search
CPC .......... A61M 16/0825; A61M 16/0833; A61M 16/0875; A61M 16/0883; A61M 16/1085; A61M 16/109; A61M 16/1095; A61M 11/041; A61M 11/042; A61M 2205/3368; F24F 2006/008; F24F 6/12; F24F 6/14; F24F 13/081; Y10S 128/909; Y10S 128/911; Y10S 128/912; Y10S 128/913; F15D 1/02; F15D 1/04; F15D 1/06
USPC .......................................................... 138/39
See application file for complete search history.

(56) References Cited

U.S. PATENT DOCUMENTS

| | | | | |
|---|---|---|---|---|
| 4,714,078 A | * | 12/1987 | Paluch | ........... A61M 16/165 |
| | | | | 128/203.17 |
| 5,054,819 A | * | 10/1991 | Grunwald | ........... F16L 43/001 |
| | | | | 285/133.11 |
| 5,213,138 A | * | 5/1993 | Presz, Jr. | ................ F15D 1/04 |
| | | | | 138/37 |
| 2002/0100320 A1 | | 8/2002 | Smith et al. | |
| 2003/0066526 A1 | * | 4/2003 | Thudor | ................ A61M 16/08 |
| | | | | 128/203.26 |
| 2007/0157928 A1 | * | 7/2007 | Pujol | .................... A61M 16/16 |
| | | | | 128/204.14 |
| 2009/0056713 A1 | * | 3/2009 | Cortez, Jr. | ........... A61M 16/08 |
| | | | | 128/203.26 |
| 2013/0112201 A1 | * | 5/2013 | Graham | ........... A61M 16/0875 |
| | | | | 128/203.27 |
| 2013/0248044 A1 | * | 9/2013 | Shiga | ..................... F15D 1/04 |
| | | | | 138/156 |
| 2017/0197057 A1 | * | 7/2017 | Osborne | ........... A61M 16/0816 |

* cited by examiner

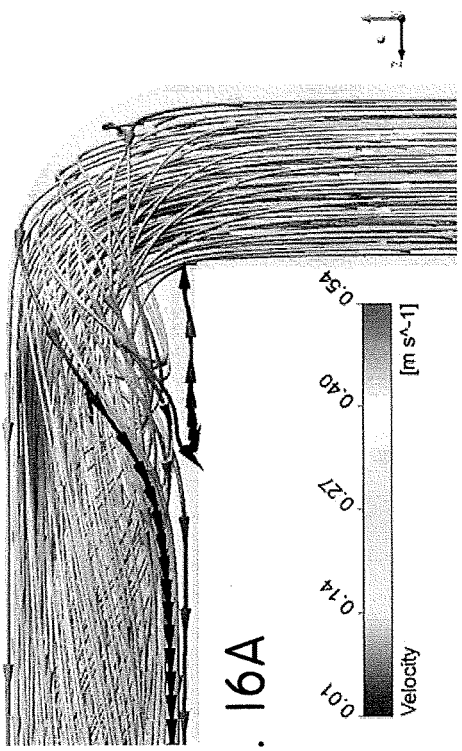
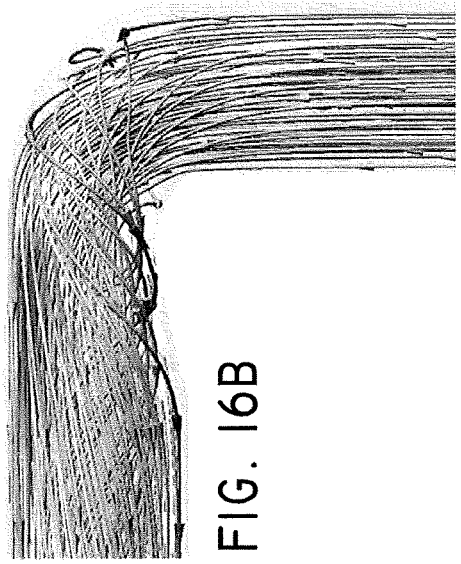
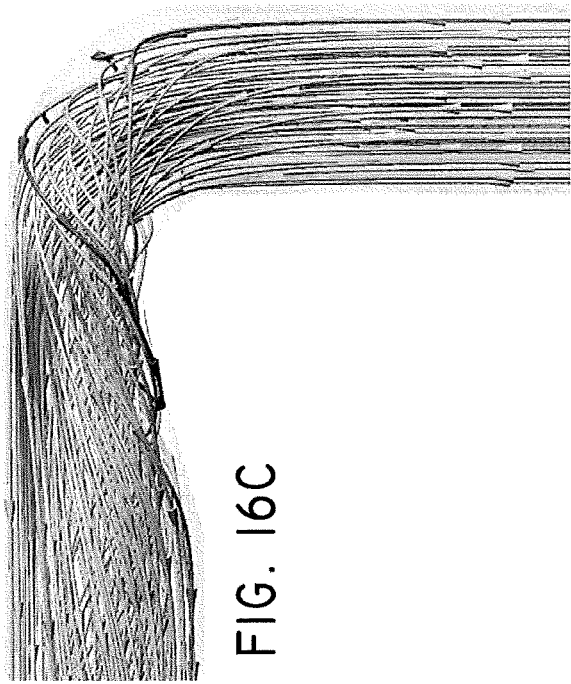

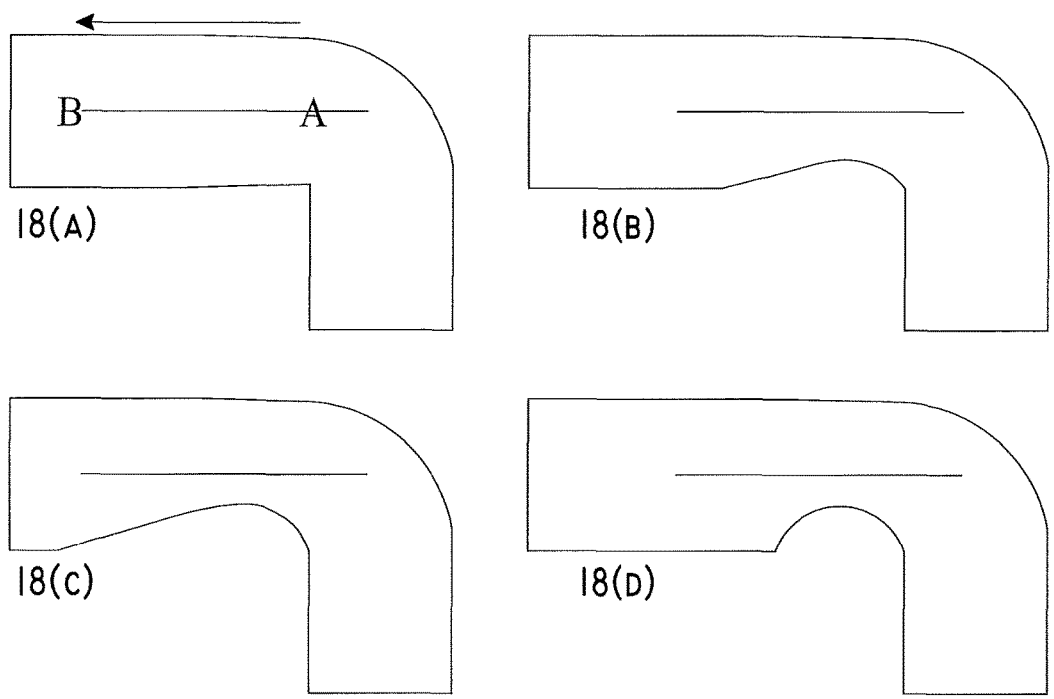
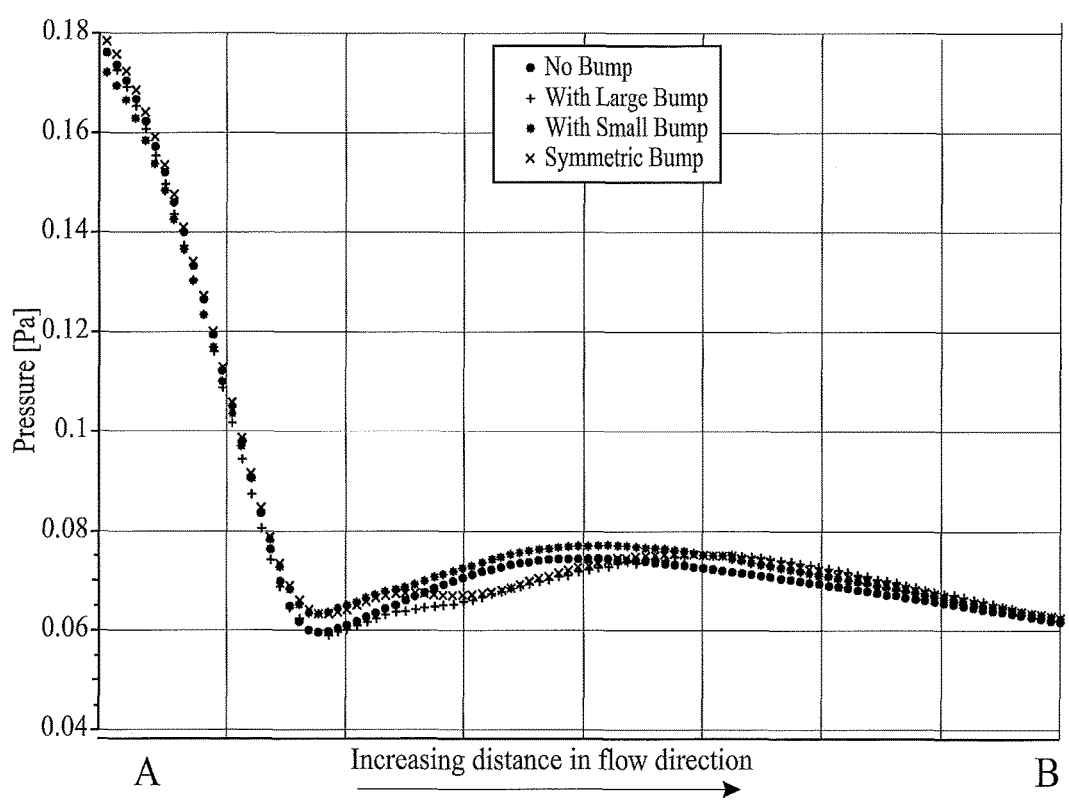
FIG. 18

RESPIRATORY HUMIDIFICATION SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Technical Field

The present disclosure generally relates to humidification systems for providing humidified respiratory gases to patients. More particularly, the present disclosure relates to features that improve the performance of humidification systems.

Description of the Related Art

Respiratory humidification systems deliver heated and humidified gases to a patient via a patient interface. Patient interfaces can include a face mask, oral mask, nasal mask, nasal cannula, a combination of oral and nasal mask, tracheal mask, or the like. Gases leaving the humidification chamber to be delivered to a patient are at a temperature and relative humidity that may mimic the transformation of air that occurs as it passes through the nose to the lungs. This promotes efficient gas exchange and ventilation in the lungs, which aids defence mechanisms in the airways and increases patient comfort during treatment. Condensation within the humidification system can occur when gases with high humidity come into contact with a component having cooler walls.

SUMMARY

Delivery of humidified gases to patients exists in the prior art, however an aspect of at least one of the embodiments disclosed herein includes the realisation that there are problems with the delivery of this humidified gas. Horizontal connectors that connect between a humidification chamber and a conduit may allow condensate from the conduit or patient interface to run back into the humidification chamber in use. Elbow ports can be used to form a horizontal connection between a humidification chamber and a conduit, which can cause recirculation to occur resulting in stagnant zones, which cause greater heat loss to occur in these regions. This results in regions of low temperatures, which are more likely to form condensate. Condensate may also form at the connector, as this is an unheated section of the gas pathway. Condensate at the connector may form at the inner surface of the outer wall, before pooling at the base of the conduit, where it may flow back to the humidification chamber.

A system is disclosed which may improve the fluid characteristics of the respiratory gas. Thus, it may reduce the amount of condensate. In some configurations, certain aspects can reduce the amount of condensate that flows back to the humidification chamber relative to the prior art. In some configurations, the angle of the elbow port can be increased to greater than 90° to reduce the recirculation that causes stagnant zones to occur and thereby reduce the condensate that forms in the system. Some embodiments include an insert or other structure shaped as a raised portion, which can be located near the sharp corner of the elbow port, to fill at least some of the dead space that is formed due to the recirculation of gases that occurs. The insert may reduce the likelihood of recirculation occurring in this region and thus may reduce the likelihood of stagnant zones forming. Therefore, regions of low temperature and low velocity gas are reduced, which reduces the amount of condensate that is generated. A raised portion may also act as barrier to any condensate that is formed and, as such, reduce the likelihood of condensate flowing back to the humidification chamber. A raised portion may be added to the port of the humidification chamber, may be part of the connector that inserts when the connector is connected to the port, or may be part of the conduit.

Some embodiments may comprise either the humidification chamber outlet port or the conduit being shaped in such a way that, or including geometries such that, gravity may reduce the likelihood of condensate reaching the humidification chamber.

Therefore, the improved system may reduce condensate formation between the outlet port of the humidification chamber and the proximal conduit end by improving flow characteristics. The improved system may provide mechanisms to reduce the likelihood of condensate flowing back to the humidification chamber.

In some configurations, a respiratory humidification system comprises a humidification chamber that comprises an outlet port; a conduit that comprises a connector configured to engage with the outlet port such that the conduit forms a gases flow path from the humidification chamber; and a raised portion located in the gases flow path directly adjacent to a sharp corner disposed along the gases flow path within a region defined between the body of the humidification chamber and the conduit.

In some such configurations, the raised portion inhibits liquid flowing from the conduit to the humidification chamber in use.

In some such configurations, the raised portion fills or at least partially fills a dead space region in the gases flow path in use.

In some such configurations, the outlet port comprises a vertical section and a horizontal section and the connector is configured to engage with the horizontal section.

In some such configurations, the raised portion is located within the horizontal section of the outlet port.

In some such configurations, the outlet port comprises a vertical section, the connector comprises a vertical section and a horizontal section, and the vertical section of the connector is configured to engage with the outlet port.

In some such configurations, the raised portion is located within the horizontal section of the connector.

In some such configurations, the raised portion is directly attached to the outlet port.

In some such configurations, the raised portion is directly attached to the connector.

In some such configurations, the raised portion is attached to the conduit.

In some such configurations, the conduit comprises one or more heating elements.

In some configurations, a respiratory humidification system comprises a humidification chamber configured to contain a volume of liquid. The humidification chamber has an outlet port. A conduit is connectable to the outlet port of the humidification chamber. The conduit and the outlet port of the humidification chamber are connected by a connector. A gases flow path is defined from an entrance to the outlet port of the humidification chamber to an outlet of the conduit. A sharp corner is positioned along the gases flow path at a location where the gases flow path makes an abrupt change in direction. A raised portion is located in the gases flow path directly adjacent to the sharp corner.

In some such configurations, the raised portion is located immediately downstream from the sharp corner.

In some such configurations, the raised portion is located within a region of the gases flow path that would be a recirculation region without the raised portion present.

In some such configurations, the raised portion forms a portion of the outlet port.

In some such configurations, the raised portion forms a portion of the connector.

In some such configurations, the raised portion forms a portion of the conduit.

In some such configurations, the raised portion fills at least a lower portion of at least one of a horizontal portion of the outlet port, a conduit or a connector such that condensate is less likely to flow from the conduit into the humidification chamber.

In some such configurations, the raised portion has a tapered edge.

In some such configurations, the raised portion has a straight edge.

In some such configurations, the raised portion is asymmetrical along its length.

In some such configurations, the raised portion is symmetrical along its length.

BRIEF DESCRIPTION OF THE DRAWINGS

These and other features, aspects, and advantages of the present disclosure will be described with respect to the following figures, which are intended to illustrate and not to limit the preferred embodiments.

FIGS. 16(a)-16(c) illustrate show streamlines coloured by velocity magnitude and indicating paths taken by a zero mass particle if that particle were traveling with the flow.

FIG. 18 is a plot comparing pressure magnitudes taken along a horizontal line that extends along an axis of the configurations of FIGS. 13(a)-13(d).

DETAILED DESCRIPTION OF THE PREFERRED EMBODIMENT

Figure 1:
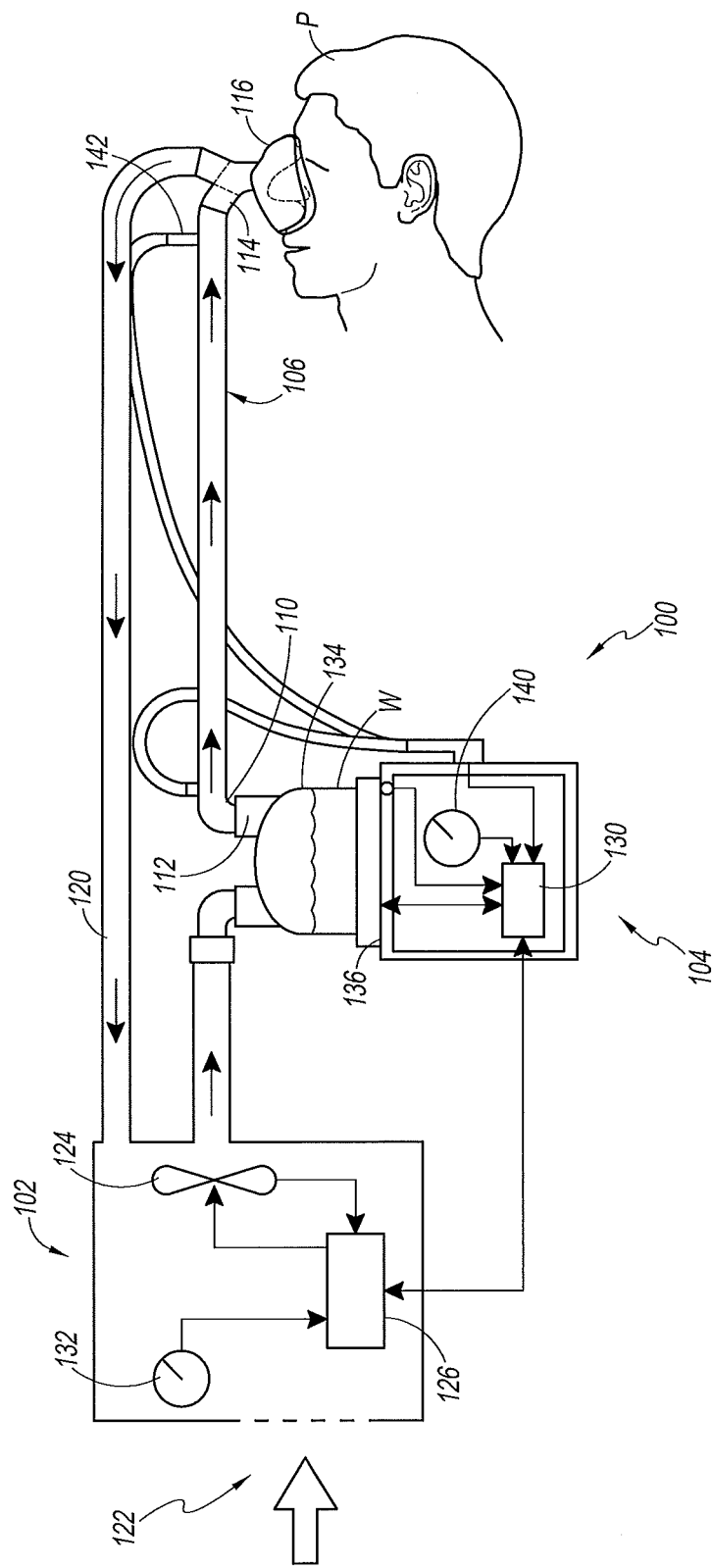
FIG. 1 is a schematic view of an example embodiment of a patient gas supply system.

With reference to FIG. 1, a system 100 is illustrated that can be used to supply heated and/or humidified gases flow to a patient or other user. The system 100 can be configured to be a continuous, variable, or bi-level positive airway pressure (PAP) system, invasive or non-invasive respiratory assistance system, high flow respiratory therapy system, a surgical insufflation system, or a system providing other forms of medical gases. The system 100 may be readily adapted for other applications involving the supply of a heated and/or humidified gas flow to a user or patient, including but not limited to laparoscopy, ventilation support, and the like. Such applications may use alternative gases, operating parameters (e.g., flow, pressure, temperature, or humidity) and patient interfaces.

In the system 100, dry or relatively dry gases pass from a gases source 102 to a humidifier 104. The gases source 102 may be, for example, a ventilator or a blower.

The humidifier 104 conditions the dry or relatively dry gases. For example, the humidifier 104 can supply heat or humidity to the dry or relatively dry gases.

An inspiratory tube 106 is used to deliver the conditioned gases to a patient P. In the illustrated configuration, a distal end 110 of the inspiratory tube 106 connects to a port 112 of the humidifier 104. Thus, the humidifier 104 supplies conditioned gases to the inspiratory tube 106.

In the illustrated configuration, the conditioned gases flow through the inspiratory tube 106 to a Y-piece 114. A patient interface 116 (e.g., a mask) receives the conditioned gases from the Y-piece 114 and the patient interface 116 supplies the conditioned gases to the patient P. Any suitable patient interface may be incorporated. Patient interface is a broad term and is to be given its ordinary and customary meaning to a person of ordinary skill in the art (that is, it is not to be limited to a special or customized meaning) and includes, without limitation, masks (such as tracheal mask, face masks, oral masks, nasal masks, a combination of oral and nasal mask, for example), cannulas (nasal cannulas, for example), and nasal pillows.

In the illustrated configuration, an expiratory tube 120 also connects to the patient interface 116 through the Y-piece 114. The expiratory tube 120 may be configured to move exhaled gases away from the patient P. In the illustrated configuration, the expiratory tube 120 returns exhaled gases from the patient P to the gases source 102.

In illustrated configuration, dry or relatively dry gases enter the gases source 102 through a vent 122 or other inlet. A fan, blower or other flow generator 124 may improve gas flow into the gases source 102 by drawing air or other gases through the vent 122. The flow generator 124 may be, for instance, a variable speed fan.

An electronic controller 126 controls the speed of the flow generator 124. In particular, the function of the electronic controller 126 may be controlled by an electronic master controller 130 in response to inputs to the master controller 130 and a user-set predetermined required value (e.g., a preset value) of pressure or fan speed. The value can be set using an input component, such as a dial 132, for example but without limitation.

The humidifier 104 comprises a humidification chamber 134. The humidification chamber 134 comprises the port 112. The body of the humidification chamber 134 can contain a volume of water W or other suitable humidifying liquid. The humidification chamber 134 is removable from the humidifier 104 after use to allow the humidification chamber 134 to be more readily sterilized or disposed.

The body of the humidification chamber 134 may be formed from a non-conductive glass or plastics material. The humidification chamber 134 may comprise conductive components. For instance, the humidification chamber 134 may comprise a highly heat-conductive base (for example, an aluminum base). The heat-conductive base can contact or associate with a heater plate 136 on the humidifier 104.

The humidifier 104 may also include electronic controls. In the illustrated configuration, the humidifier 104 includes the master controller 130. The master controller 130 can be an electronic, analog, or digital master controller. The master controller 130 may be a microprocessor-based controller executing computer software commands stored in associated memory. In response to humidity or temperature values provided via a user interface 140, for example, and other inputs, the master controller 130 determines when (or to what level) to energize the heater plate 136 to heat the water W within the humidification chamber 134.

A sensor probe 142 may connect to the inspiratory tube 106 near the Y-piece 114, or directly to the Y-piece 114 or the patient interface 116. The sensor probe 142 monitors the temperature of the flow of gases near or at the patient interface 116. A heating filament (not shown) may be used to adjust the temperature of the patient interface 116, the Y-piece 114, and/or the inspiratory tube 106 to raise or maintain the temperature of the flow of gases above the saturation temperature, thereby reducing the opportunity for unwanted condensation.

In FIG. 1, exhaled gases are returned from the patient interface 116 to the gases source 102 via the expiratory tube 120. The expiratory tube 120 may have a sensor probe and/or heating filament, as described above with respect to the inspiratory tube 106, integrated with it to reduce the opportunity for condensation. Furthermore, the expiratory tube 120 need not return exhaled gases to the gases source 102. Alternatively, exhaled gases may be passed directly to ambient surroundings or to other ancillary equipment, such as an air scrubber/filter (not shown). In certain embodiments, the expiratory tube 120 is omitted altogether.

Figure 2:
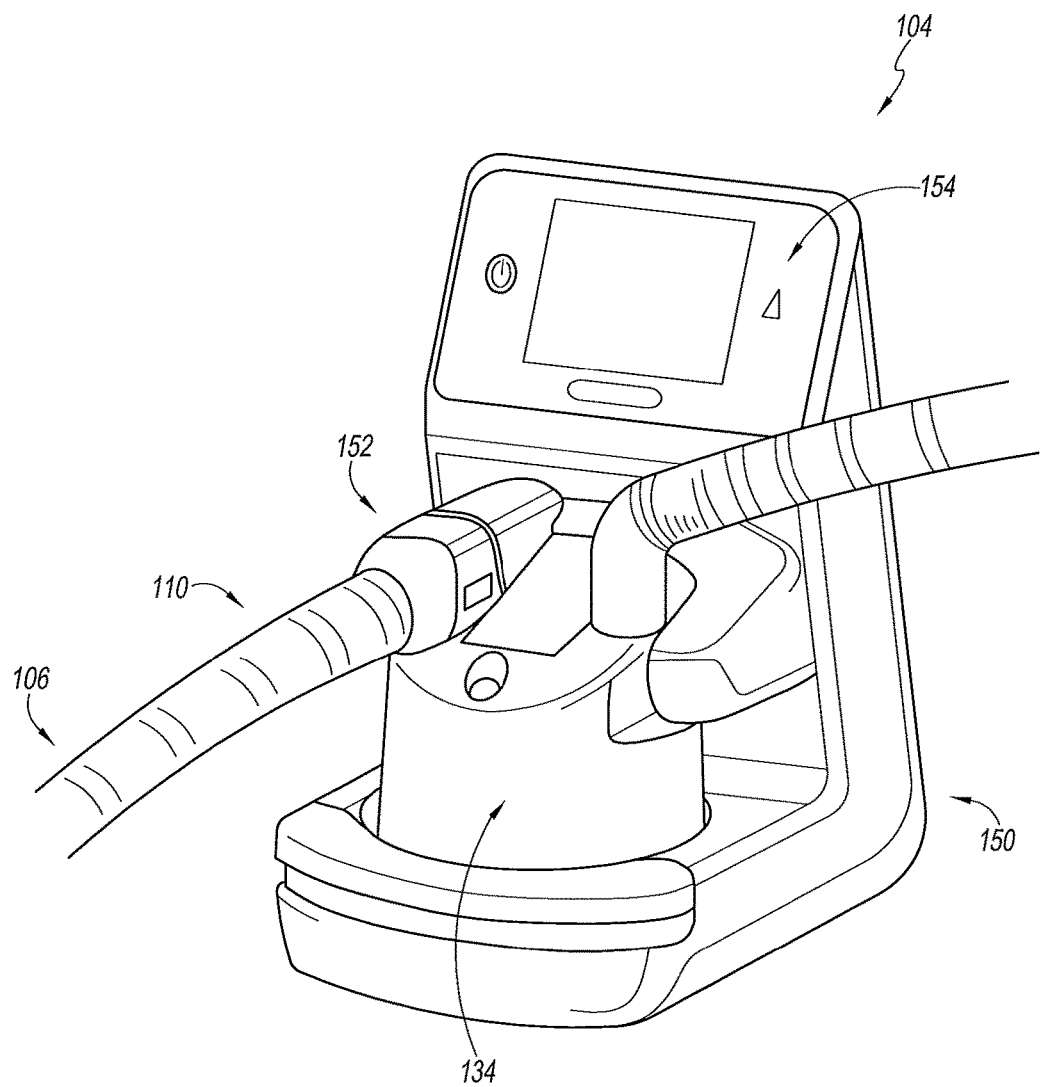
FIG. 2 is a perspective view of a humidifier useable in the system of FIG. 1.

With reference to FIG. 2, a humidification apparatus 150 that can be used as the humidifier 104 in the system 100 is shown. As illustrated, a connector 152 pneumatically connects the distal end 110 of the inspiratory tube 106 to the port (not shown) of the humidification chamber 134. The connector 152 may also facilitate electrical connection to the humidifier 104. The conduit 106 may comprise one or more resistive heating wires that provide for heating of gases flowing through the conduit 106 and/or sensor wires that electrically or otherwise facilitate communication of signals relating to one or more parameters of the system 100. Thus, the term "electrical connection" is used to distinguish from "pneumatic connection" and should not be construed in a limiting way.

The humidifier 104 further includes a panel 154. The panel 154 may be used to mount a user display and/or controls. For example, various dials, switches, and other input means may be used to control operation of the device. Additionally or alternatively, a touch screen display may be used. The user display may display parameters of the system 100, warnings in the event of any errors or malfunctions, or prompts where user action is required, etc. Where a touch screen display is used, the same display may be used to present information to a user and receive inputs from a user, at least in part.

Figure 3:
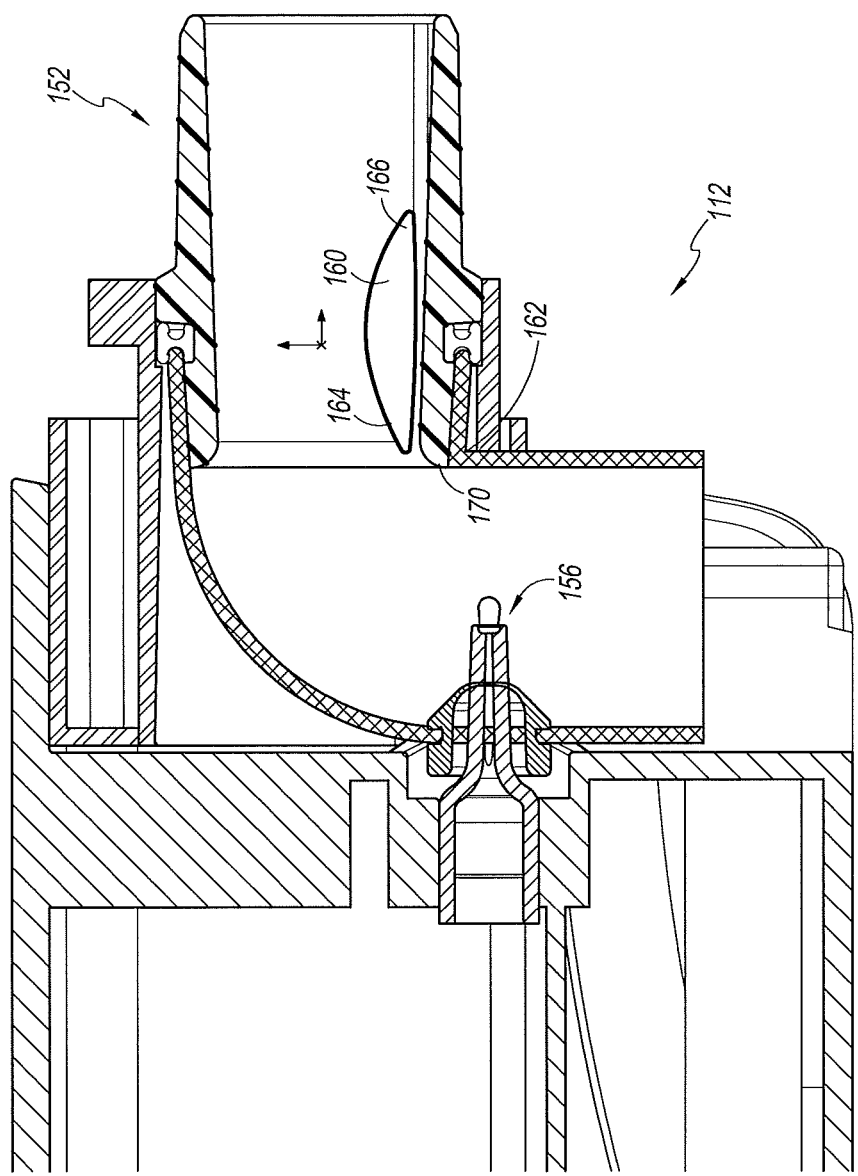
FIG. 3 in an enlarged section view of a portion of the humidifier of FIG. 2 and showing a first configuration of a raised portion within the gases flow path.

As illustrated in FIG. 2, the conduit 106 is mounted to the humidification chamber 134 such that the conduit 106 extends substantially parallel to the direction of motion of the humidification chamber 134 as it is slid on or off of the humidifier 104. With reference to FIG. 3, a sectioned view of a portion of the humidifier 104 is shown. As shown, a probe 156 can be positioned within the outlet port 112 upstream of the connector 152 that connects the chamber 134 to the inspiratory tube 106. In some configurations, the probe 156 can be positioned in the port 112. In some configurations, the probe 156 can be positioned within the connector 152. In some configurations, the port 112 is formed as an elbow with a vertically extending portion and a horizontally extending portion. Other configurations are possible.

In configurations with the elbow port 112 having a sharp corner, it has been discovered that a significant amount of recirculation occurs in the horizontal portion of the port 112. More particularly, with reference to FIGS. 7-12, a sharp corner at the inside lower transition from vertical to horizontal causes a significant amount of recirculation within the flow. This recirculation, in effect, creates a significant region of dead space. The gases flow can cool within the recirculation/dead space region, which can cause condensation to occur within this region.

FIGS. 7-12 show examples of the velocity and temperature profiles that can be generated for flow rates of 5 L/min, 30 L/min and 60 L/min respectively. The system 100 is not limited to these flow rates; they merely provide an indication of the relationship between different flow rates and the generated fluid characteristics. It appears that a larger dead space region may be generated at higher flow rates.

The system 100 disclosed herein may improve the fluid characteristics of the respiratory gas and may reduce the amount of condensate or other fluid that flows back to the humidification chamber 134 from the attached conduit 106. To improve the fluid characteristics in the system 100, the angle of the elbow port 112 of the humidification chamber 134 may be increased; this may soften the sharp corner that is shown in FIGS. 7-12.

Figure 4:
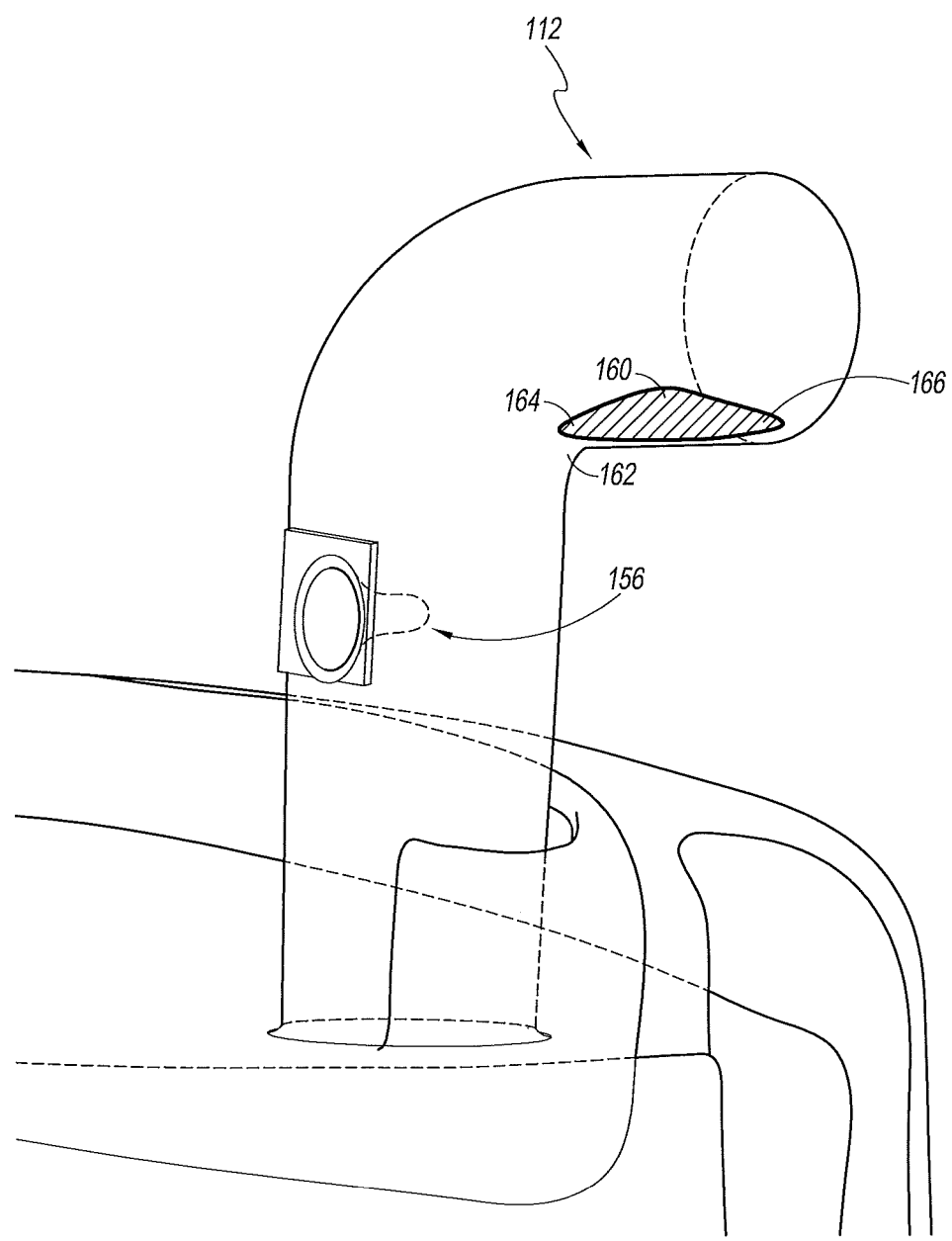
FIG. 4 is a view of a portion of a humidifier chamber useable with the humidifier of FIG. 2 and showing a second configuration of a raised portion within the gases flow path.

With reference again to FIG. 3, a raised portion (or insert) 160 can be attached to, or integrally formed with, one or more components of the system 100. For example, the raised portion 160 is shown in FIG. 3 as being positioned within the connector 152. By way of another example, the raised portion 160 is shown in FIG. 4 as being positioned within the port 112. In some configurations, the raised portion 160 can be positioned within the inspiratory conduit 106 or the like. The raised portion 160 may be inserted or added to a component using moulding techniques, adhesives, or other appropriate ways of attachment.

In some configurations, an elbow portion 162 can be defined at the transition from a first direction to a second direction of the port 112. In some configurations, the elbow portion 162 is defined by a transition from a first direction to a second direction that is generally normal to the first direction. In some configurations, the elbow portion 162 is defined by a transition from vertical to horizontal.

As shown in FIG. 3 and FIG. 4, the raised portion 160 can be positioned directly adjacent to the elbow portion 162. As used herein, directly adjacent has its ordinary meaning of sharing a border or boundary. In some configurations, the raised portion 160 is positioned within the gas flow of only one of the two portions of the port 112. In other words, in the illustrated configurations, the raised portion 160 protrudes into the gas flow path of the horizontal portion but does not protrude into the gas flow path of the vertical portion. In some configurations, at least the upstream end 164 of the raised portion 160 is positioned entirely within a region that would be a recirculation region without the raised portion 160 present. In some such configurations, both the upstream end 164 and the downstream end 166 of the raised portion 160 are positioned within a region that would be a recirculation region without the raised portion 160 present. In some configurations, the entire raised portion 160 is positioned within a region that would be a recirculation region without the raised portion 160 present. In some configurations, the raised portion 160 is located in the gases flow path directly adjacent to a sharp corner 170 created by the angle of the elbow portion 162 disposed along the gases flow path within a region defined between the humidification chamber 134 and the conduit 106. In some configurations, the sharp corner 170 is positioned along the gases flow path at a location where the gases flow path makes an abrupt change in direction.

Figure 5:
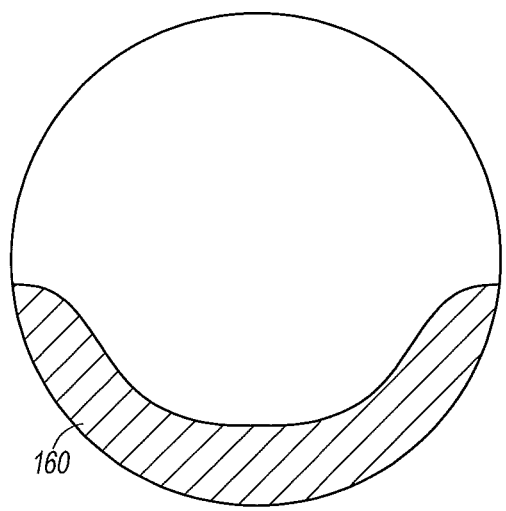
FIGS. 5 and 6 show cross-sections of raised portions.
Figure 6:
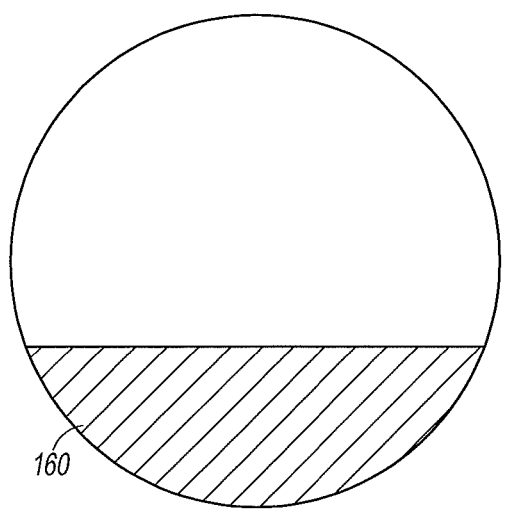
Figure 7:
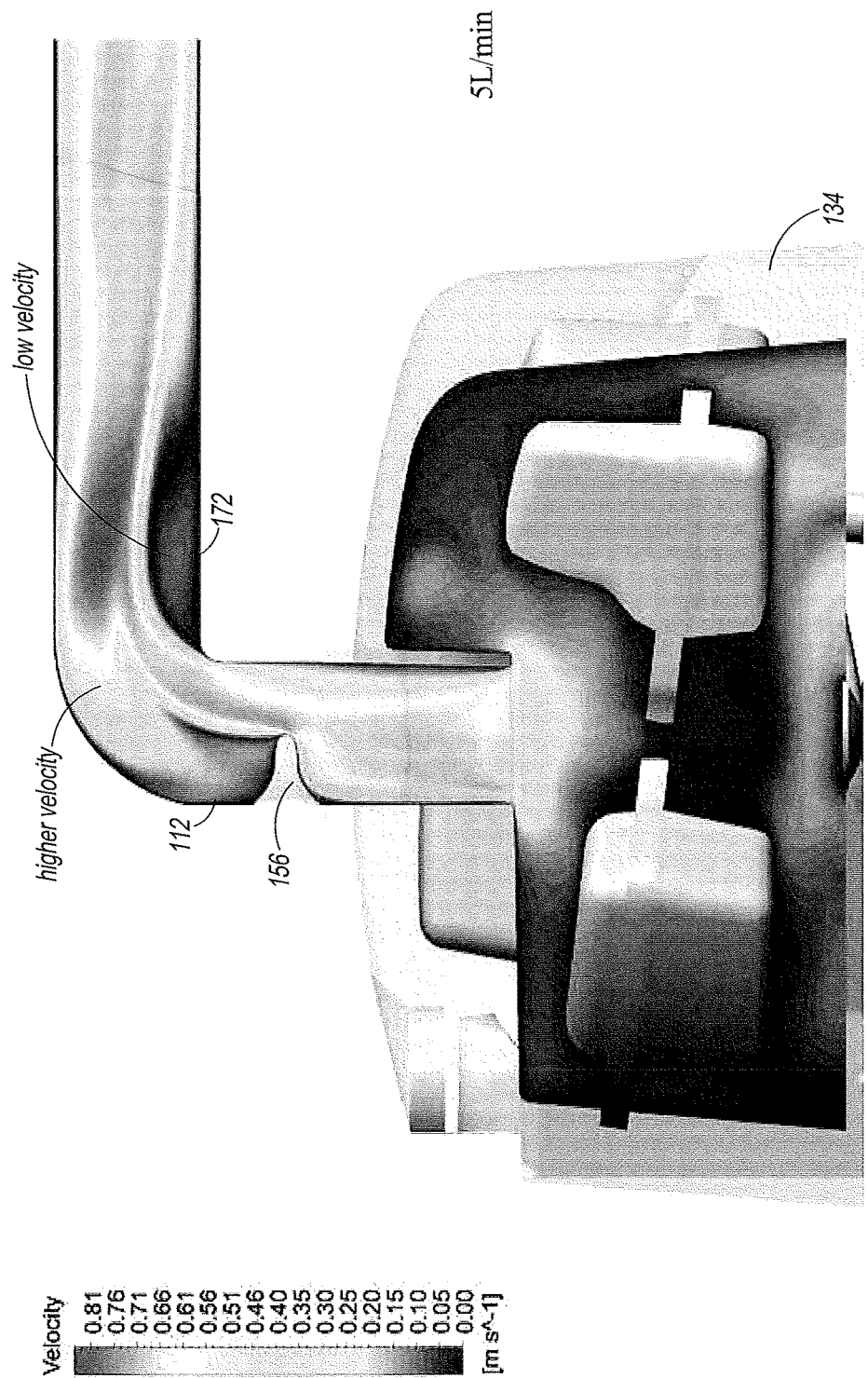
FIG. 7 shows a velocity profile of a humidification chamber with an elbow port for a 5 L/min flow.
Figure 8:
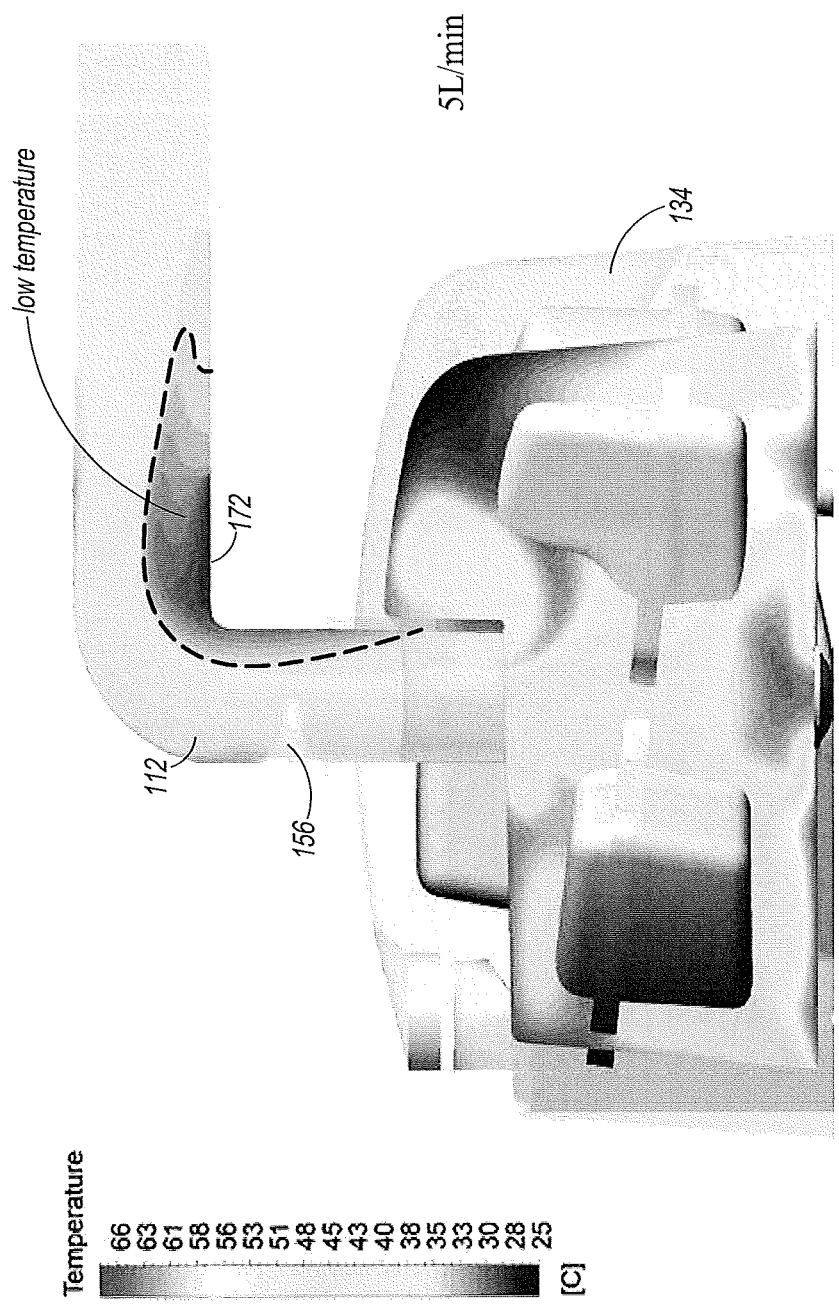
FIG. 8 shows a temperature profile of a humidification chamber with an elbow port for a 5 L/min flow.
Figure 9:
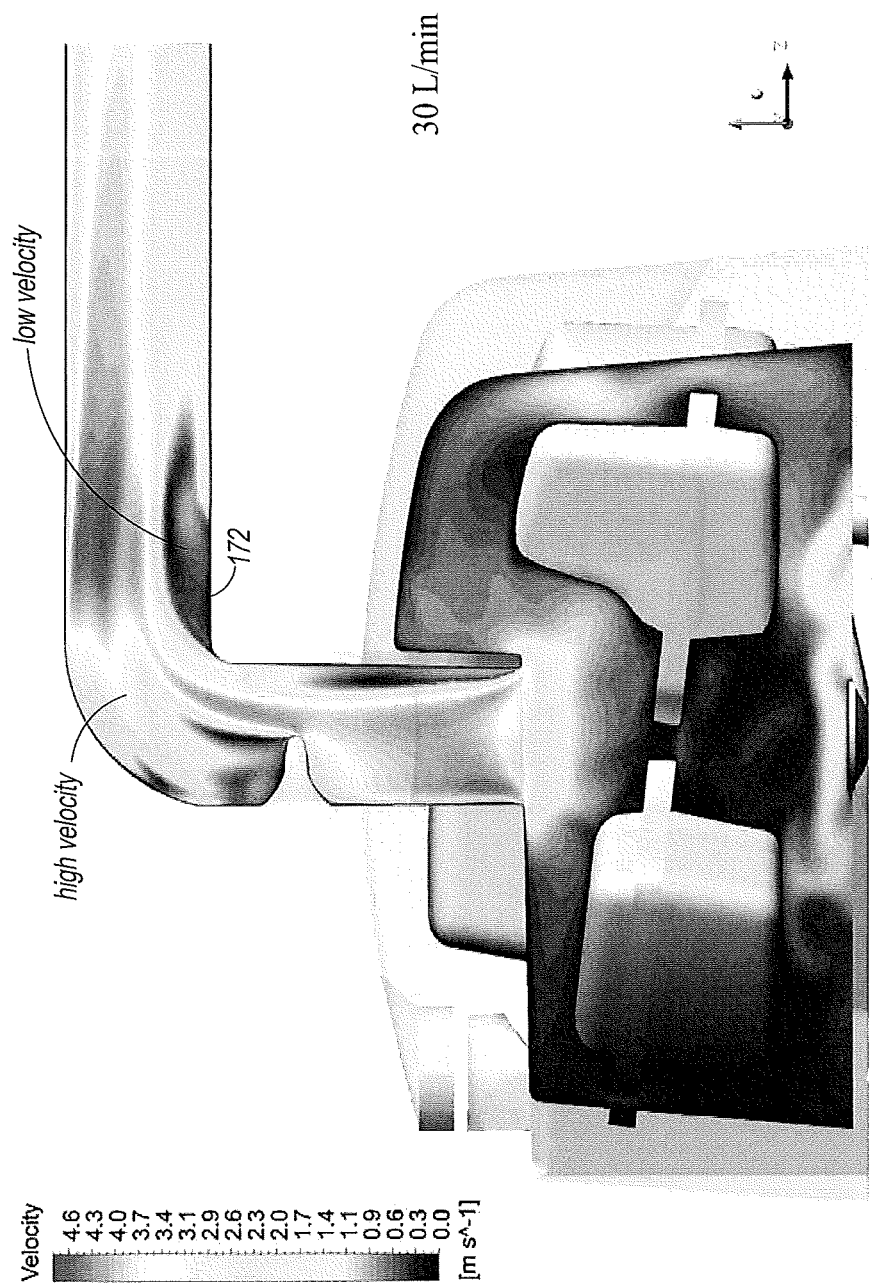
FIG. 9 shows a velocity profile of a humidification chamber with an elbow port for a 30 L/min flow.
Figure 10:
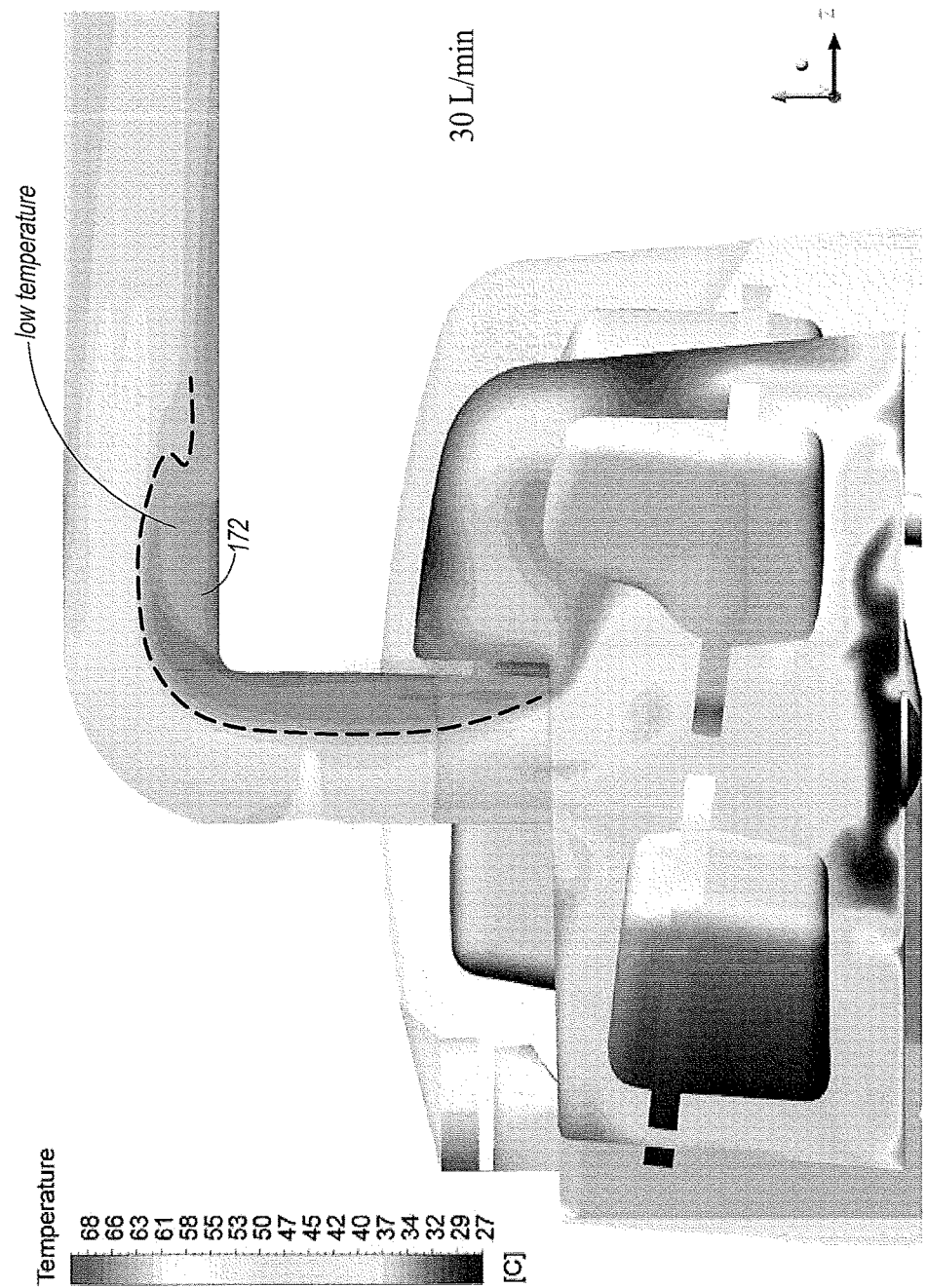
FIG. 10 shows a temperature profile of a humidification chamber with an elbow port for a 30 L/min flow.
Figure 11:
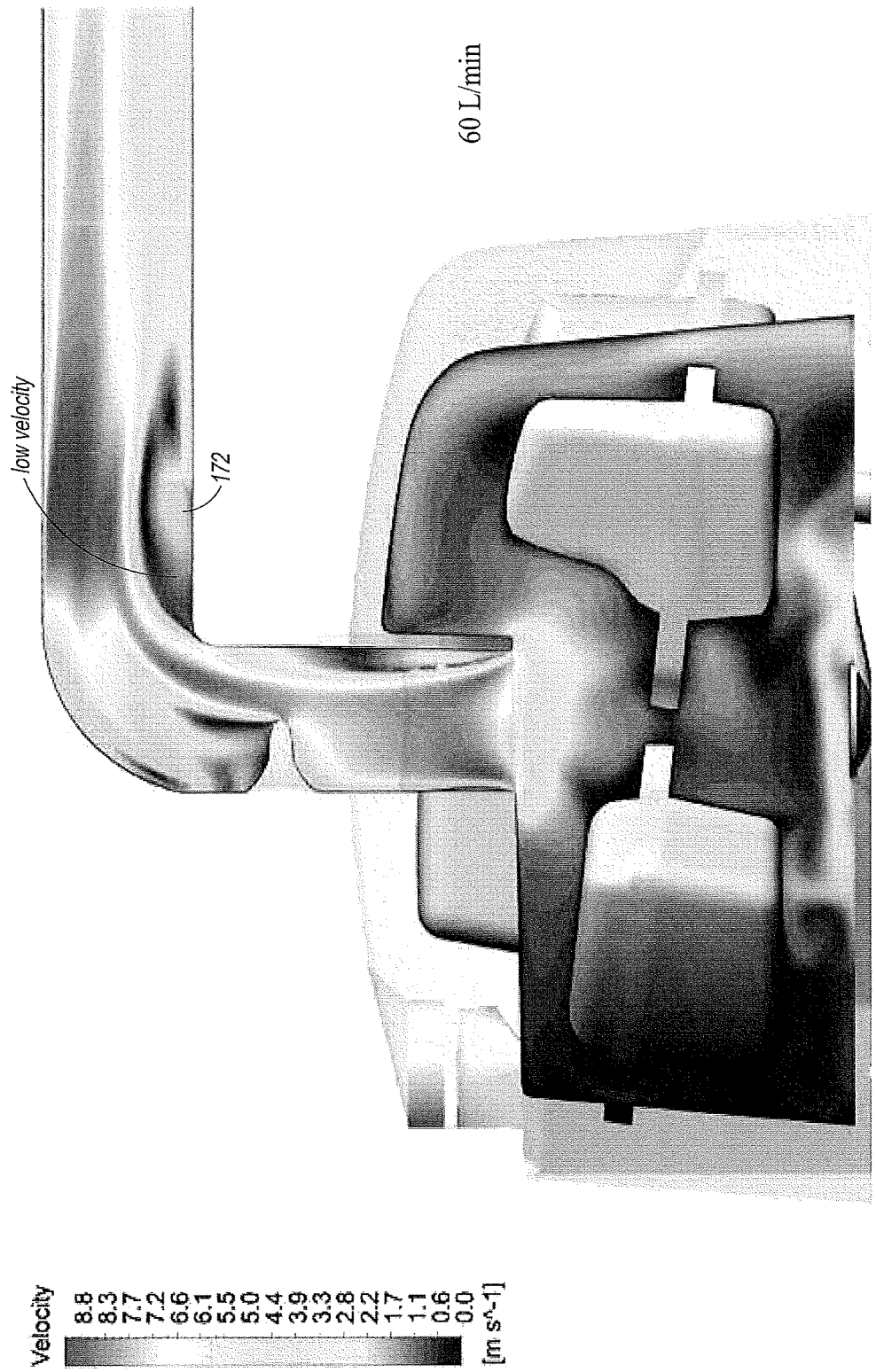
FIG. 11 shows a velocity profile of a humidification chamber with an elbow port for a 60 L/min flow.
Figure 12:
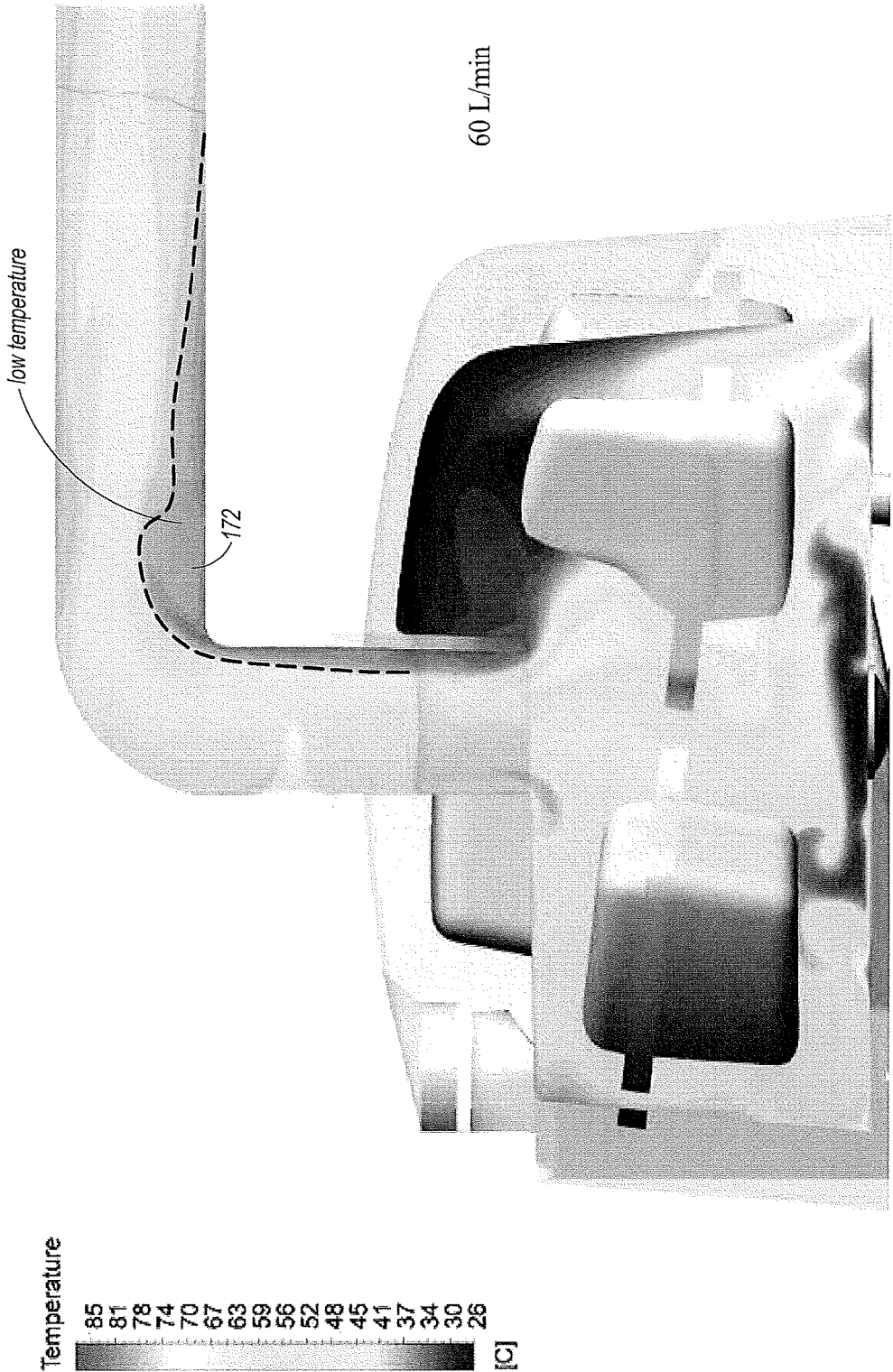
FIG. 12 shows a temperature profile of a humidification chamber with an elbow port for a 60 L/min flow.

With reference now to FIG. 5 and FIG. 6, the raised portion 160 may resemble a speed bump, protrusion, insert, or the like. The raised portion 160 can be integrally formed with the port 112, the connector 152, or another component that joins the humidification chamber 134 and the inspiratory conduit 106. The raised portion 160 can be a separate and/or separable component from the port 112, the connector 152, or other component and secured thereto in any suitable manner.

As shown in FIG. 4, the raised portion 160 is attached to the outlet port 112 of the humidification chamber 134. The outlet port 112 comprises the elbow portion 162, which, in this case, creates an angle of, but not limited to, 90°. The raised portion 160 is located at or near the sharp corner 170 created by the angle of the elbow portion 162 because the fluid may be more likely to follow the surface of the port 112 if it is a smooth curve.

The size of the raised portion 160 can be determined by the temperature and velocity profiles, examples of which are shown in FIGS. 7-12, which estimate the size of a dead space region 172 present in the system 100 at high flows. As discussed above, the dead space region 172 may appear to be larger at higher flow rates and, therefore, if the raised portion 160 is made to accommodate these flow rates, it may also accommodate lower flow rates. Occlusion of flow is less likely to occur at lower flow rates and, because the raised portion 160 fills the regions of otherwise dead space present in the system 100, there are minimal limitations of flow. Thus, the raised portion 160 may accommodate higher flow rates, although, in some embodiments, lower flow rates may also be accommodated. The system 100 discloses the use of the raised portion 160 to accommodate flows between about 5 L/min and about 60 L/min. Some embodiments may accommodate flow rates that exceed these values, for example between 0 L/min and about 100 L/min.

FIG. 3 shows the raised portion 160 inserted into the port 112 as the connector 152 is connected with the humidification chamber port 112. The raised portion 160 may be attached to the connector 152, the raised portion 160 may be attached to the conduit 106 or, in some embodiments, the raised portion 160 may act as a tongue that may be attached to the connector 152 or the conduit 106 and that may extend past the edge of the connector 152 into the outlet port 112. In some embodiments, the connector 152 may be a male connector that is used with the raised portion 160 attached at the edge of the connector 152. This is not considered to be an exhaustive list of mechanisms to insert the raised portion 160 into the port 112 of the humidification chamber 134, but merely a listing of examples of mechanisms that could be used, recognising that other mechanisms may also be possible.

The raised portion 160 may be located near the sharp corner 170 to soften the sharp corner 170 and to fill at least a portion of, if not the entirety of, the dead space region 172 that is formed (see FIGS. 7-12). Benefits of inserting the raised portion 160 into the port 112 of the humidification chamber 134 as the connector 152 is inserted include the reduced distance between the outlet port 112 of the humidification chamber 134 and the conduit 106. This may be beneficial because the connector 152 itself is unheated, which allows the gas to cool therein, which can cause the formation of condensate as the gas travels between the outlet port 112 of the humidification chamber 134 and the conduit 106. By reducing the distance between the outlet port 112 of the humidification chamber 134 and the heated portion of the conduit 106, the time available for gas cooling may be reduced. As a result, the amount of condensate that is formed may also be reduced.

The raised portion 160 may also act to occlude some or all of any condensate or other liquid flowing back into the humidification chamber 134. By filling at least a portion of the dead space 172, the lower temperature zone of recirculation can be reduced and, thus, it is likely that less condensate is generated due to the reduced flow separation that may be produced. This may improve the temperature profile of the gas over the unheated connector 152 as it moves towards the heated conduit 106, which may result in less temperature loss as it passes through the unheated connector 152.

FIG. 5 and FIG. 6 show possible cross sections of the raised portion 160, such as that discussed above. FIG. 5 shows the raised portion 160 having a tapered edge while FIG. 6 shows the raised portion 160 having a straight edge. Other configurations also are possible.

With reference to FIGS. 13(a)-13(d), several different configurations that have been investigated are illustrated. Note that FIGS. 13(a)-13(d) are depictions of the gases flow path and, as such, the raised portion 160 is not explicitly shown and the conduit 106, the connector 152, and the port 112 also are not explicitly shown. Rather, these illustrations simply reflect the gas flow path defined by these boundary components.

Figure 13B:
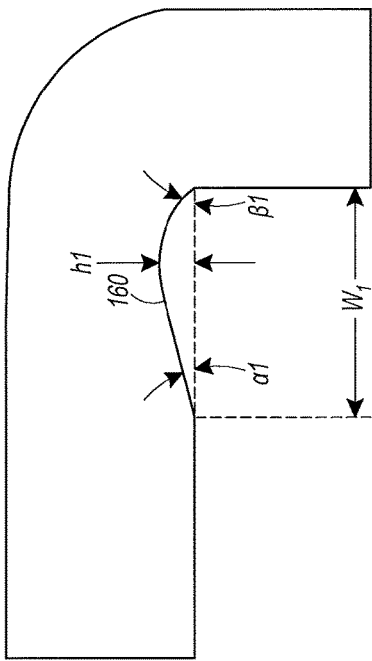
FIGS. 13(a)-13(d) show different configurations of gas flow paths with three different raised portions illustrated in FIGS. 13(b)-13(d).
Figure 13D:
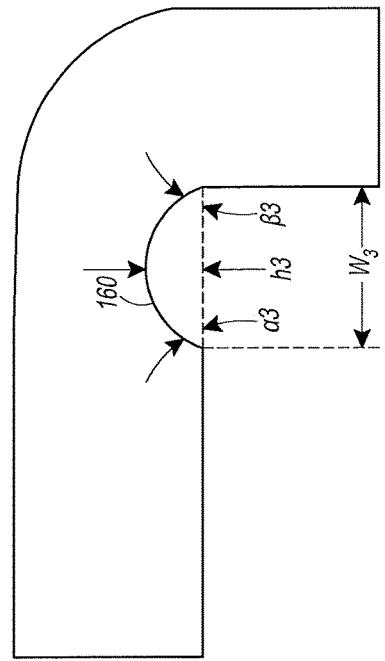
Figure 13A:
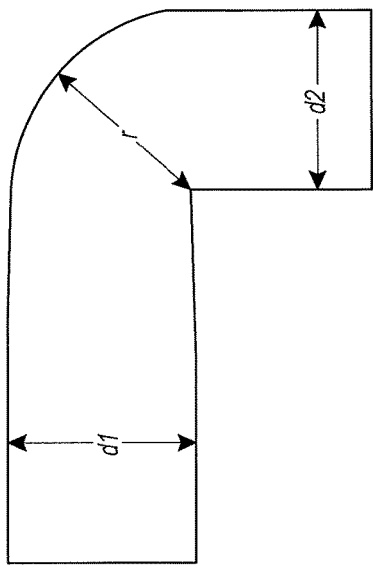

FIG. 13(a) illustrates a configuration without any raised portion. FIG. 13(a), however, is useful to establish a baseline and to explain some of the dimensions used in the following discussion. As illustrated, the flow path has an outlet diameter d1 and an inlet diameter d2. In some configurations, the outlet diameter and the inlet diameter are the same. In some configurations, the outlet diameter d1 is larger than the inlet diameter d2 (i.e., the conduit 106 has a larger bore diameter than the port 112). In the illustrated configurations, the inlet diameter d2 is 20 mm while the outlet diameter d1 is 21 mm. Also, in the illustrated configurations, the radius r between the inlet portion and the outlet portion is 10 mm. In each of the configurations shown in FIGS. 13(a)-13(d), these basic dimensions are the same.

Figure 13C:
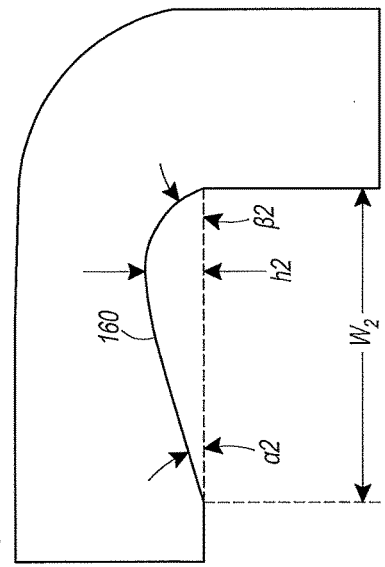
Figure 14B:
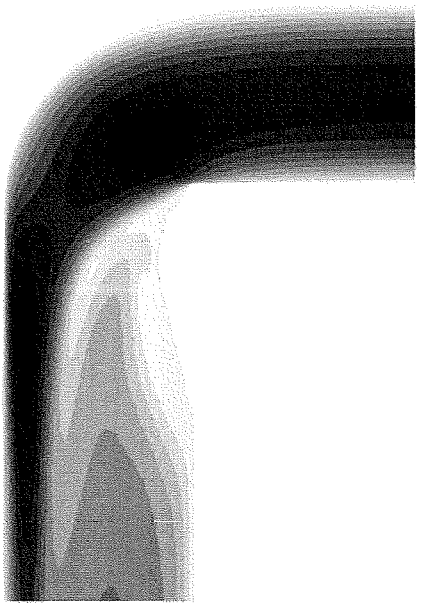
FIGS. 14(a)-14(d) illustrate flow velocity contours through the configurations of FIGS. 13(a)-13(d) for a 5 L/min flow.
Figure 14D:
Figure 14A:
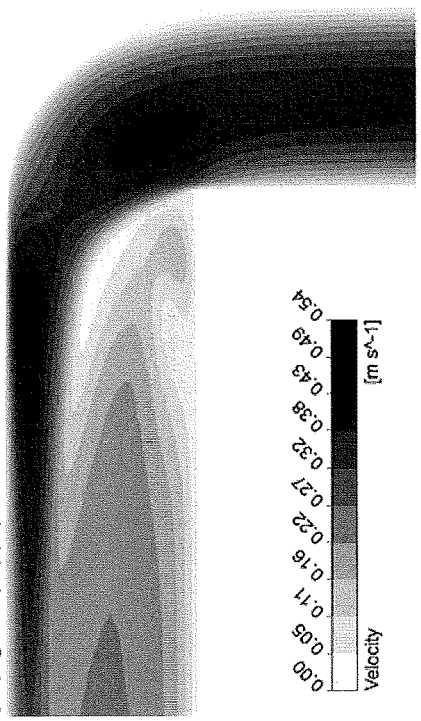
Figure 14C:
Figure 15B:
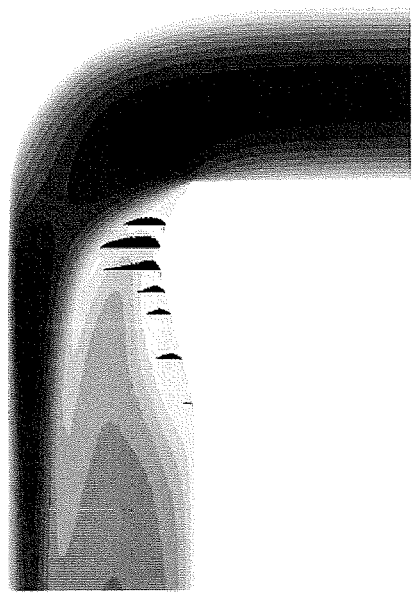
FIGS. 15(a)-15(d) illustrate reverse flow vectors overlaid onto the flow velocity contours of FIGS. 14(a)-14(d).
Figure 15D:
Figure 15A:
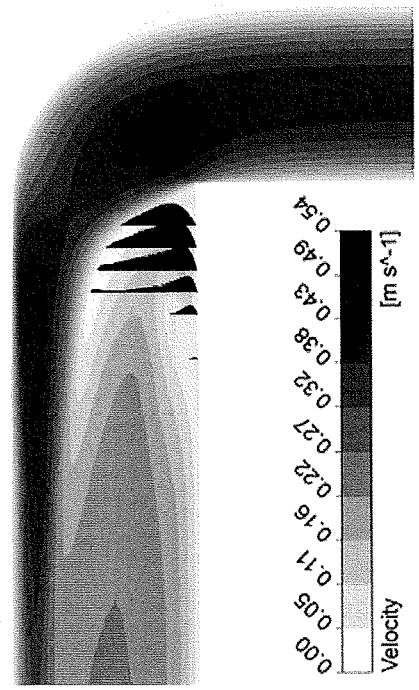
Figure 15C:
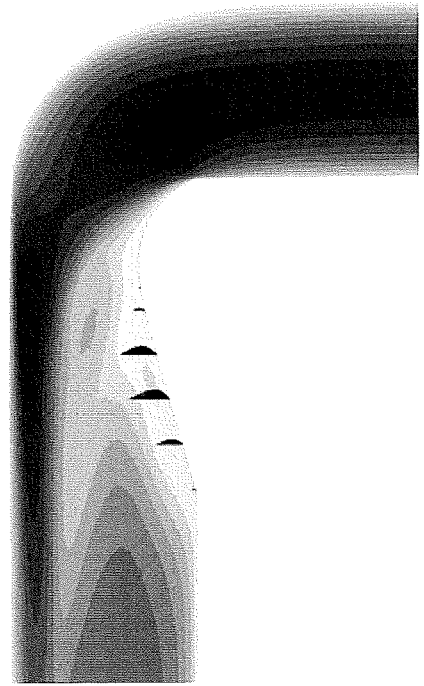

FIG. 13(b) illustrates a smaller asymmetric embodiment of the raised portion 160. FIG. 13(c) illustrates a larger asymmetric embodiment of the raised portion 160. FIG. 13(d) illustrates a symmetric embodiment of the raised portion 160. With reference to FIGS. 13(b), 13(c), and 13(d), each of the raised portions 160 can be generally defined in section with the illustrated dimensions. Each of the raised portions 160 will have a first angle (α) at the downstream end 166, a second angle (β) at the upstream end 164, a length (w) and a height (h). A volume reduction in the flow path in the region of the raised portions 160 can be defined as the volume of the raised portion 160 divided by the volume of the cylinder bounded by the length (w) of the raised portion 160 and the outlet diameter (d1).

In some configurations, the first angle (α) can be determined once the other dimensions have been determined. For example, in some configurations, the height (h) can be between 15% and 30% of the outlet diameter d1. The second angle (β) can be between 30° and 60°. The length (w) can be larger than 18 mm. Thus, the upper limit of the length (w) and the corresponding range for the first angle (α) can be a function of the other values. In some configurations, however, the first angle (α) can be between 50° and 70°. In some configurations, the first angle (α) can exceed 60° such that condensate is more likely to be contained within the conduit 106 rather than flowing back into the humidification chamber 134.

With reference now to FIG. 13(b), the height (h) of the illustrated raised portion 160 is 4 mm. The length (w) of the raised portion 160 is 25 mm. The first angle (α) of the raised portion 160 is 15 degrees and the second angle (β) is 35 degrees. The illustrated raised portion 160 creates a volume reduction of 4%.

With reference now to FIG. 13(c), the height (h) of the illustrated raised portion 160 is 6 mm. The length (w) of the raised portion 160 is 35 mm. The first angle (α) of the raised portion 160 is 15 degrees and the second angle (β) is 60 degrees. The illustrated raised portion 160 creates a volume reduction of 14%.

With reference now to FIG. 13(d), the height (h) of the illustrated raised portion 160 is 6 mm. The length (w) of the raised portion 160 is 18 mm. The first angle (α) of the raised portion 160 is 60 degrees and the second angle (β) is 60 degrees. The illustrated raised portion 160 creates a volume reduction of 8%.

FIGS. 14(a)-14(d) correspond to FIGS. 13(a)-13(d) and demonstrate the effect on the flow velocity in each configuration. FIGS. 14(a)-14(d) are flow velocity contours at a flow rate of 5 LPM. The contours of the no raised portion configuration of FIG. 14(a) clearly show that the elbow portion 162 creates an area of lower velocity gases, and it is in this area that the gases can cool. Each of the raised portions 160 of FIGS. 14(b)-14(d) has a positive effect on flow velocity, especially on velocities in the middle of the range. In addition, it can be seen that the more smoothly tapering asymmetric raised portions 160 of FIGS. 14(b) and 14(c) have significantly improved flow characteristics, because the shallow angle (α) of the tapering end of the raised portion 160 reduces the area of potential dead space downstream of the raised portion 160.

FIGS. 15(a)-15(d) correspond to FIGS. 13(a)-13(d) and show reverse flow vectors extending from the planes of several cross sections downstream of the elbow portion 162. These vectors are overlaid onto the flow velocity contours of FIGS. 14(a)-14(d). The vector lengths represent the magnitudes of negative flow velocity components (i.e., the velocities of flow in the reverse direction to normal flow), which are indicative of recirculation that results in cooling gases. From these illustrations, it is apparent that the regions having the reverse flow components also have the lowest velocities, so it stands to reason that reducing recirculation will improve overall flow velocity and decrease cooling of the gases. Each of the raised portions 160 reduces recirculation relative to the configuration with no raised portion. The large asymmetric raised portion 160 of FIG. 15(c) appears to reduce recirculation the most. Again, the symmetric raised portion 160 of FIG. 15(d) does not appear to improve flow characteristics as much as the asymmetric raised portions 160 of FIGS. 15(b) and 15(c).

FIGS. 16(a)-16(c) correspond to FIGS. 13(a)-13(c); there is no corresponding illustration for FIG. 13(d). FIGS. 16(a)-16(c) show streamlines coloured by velocity magnitude and indicating paths taken by a zero mass particle if that particle were traveling with the flow. As shown in these illustrations, the recirculation and low velocity zones are greater in size following the sharp corner 170 of the elbow portion 162 where there is no raised portion. In addition, the larger raised portion 160 of FIG. 16(c) appears to improve performance over the smaller raised portion 160 of FIG. 16(b).

Figure 17:
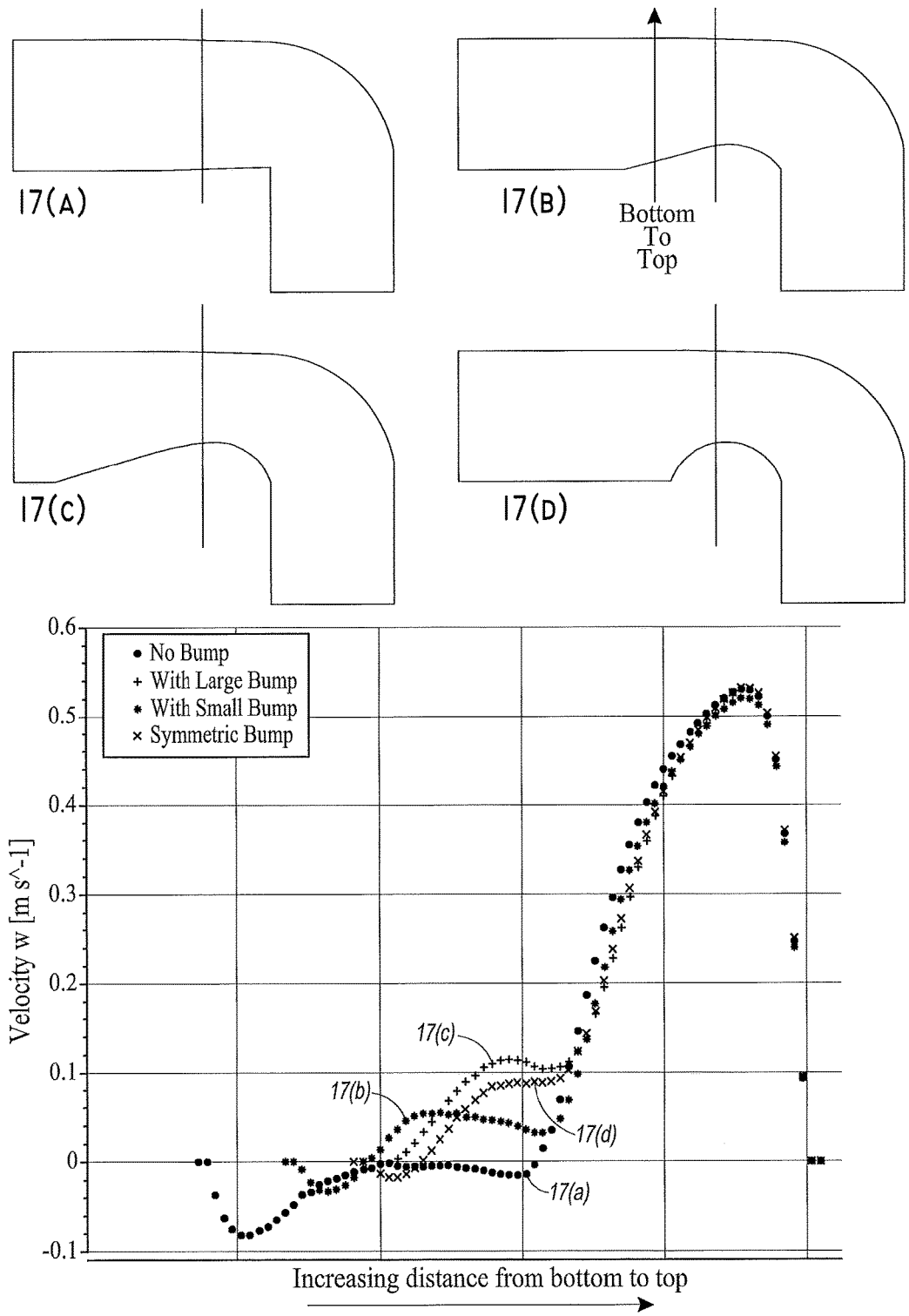
FIG. 17 is a plot illustrating the flow velocity components in a 5 LPM flow relative to the direction of flow at the same cross section for each of the configurations of FIGS. 13(a)-13(d).

FIG. 17 is a plot illustrating the flow velocity components in a 5 LPM flow relative to the direction of flow at the same cross section for each of the configurations of FIGS. 13(a)-13(d). Negative velocities indicate flow velocity components in the reverse direction compared to normal flow (i.e., recirculation). Each of the configurations demonstrates very similar velocities in the upper region of the cross-section (i.e., the right side of the plot) but there are significant differences in the lower region of the cross-section (i.e., the left side of the plot). The configuration of FIG. 13(a), which has no raised portion, demonstrates large regions of stagnation (near 0) and recirculation (below 0) before reaching the upper region and middle region, where positive flow is taking place. As shown, the larger raised portion 160 of FIG. 13(c) demonstrates the most improvement to reducing or eliminating recirculation and/or stagnant flow.

FIG. 18 is a plot comparing pressure magnitudes taken along a horizontal line that extends along an axis of the configurations of FIGS. 13(a)-13(d). As shown in the plot of FIG. 18, the pressure drop, and therefore the resistance to flow, remains very similar for all four of the designs of FIGS. 13(a)-13(d). As such, the benefits of recirculation reduction can be obtained without significantly impacting resistance to flow.

Figure 19A:
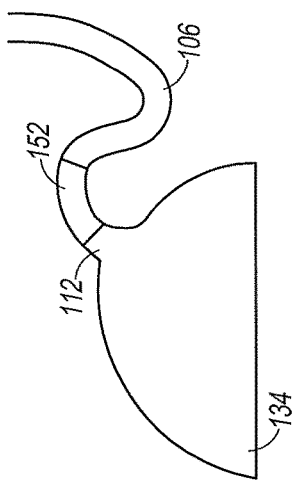
FIGS. 19(a)-19(d) show additional humidification chamber embodiments designed to impede condensate flowing back into the humidification chamber.
Figure 19B:
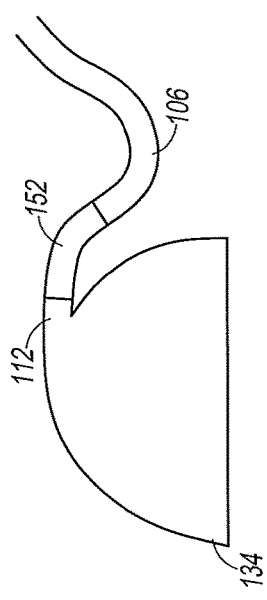
Figure 19C:
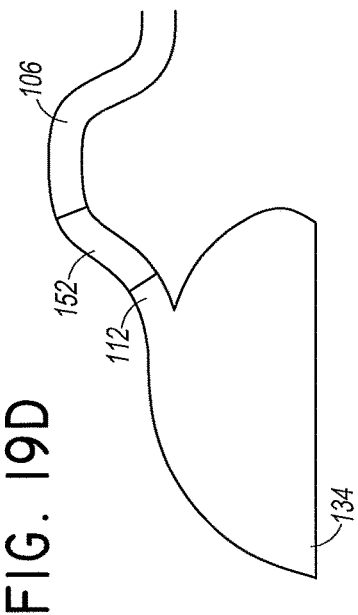
Figure 19D:
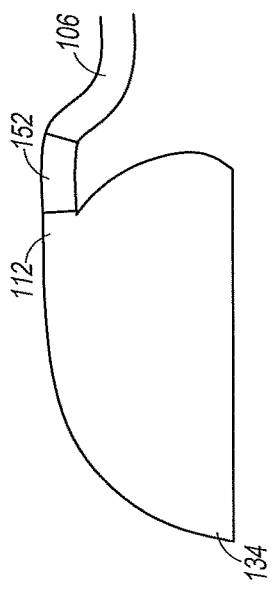

In addition to improving flow characteristics, the raised portions 160 provide the advantage of thwarting the flow of condensate back into the chamber 134. In configurations desiring to take advantage of this characteristic, the symmetrical raised portion 160 of FIG. 13(d) provides enhanced performance over the asymmetrical raised portions 160 of FIGS. 13(b) and 13(c). In addition, configurations as shown in FIGS. 19(a)-19(d) use different geometries to allow gravity to reduce the likelihood of condensate flowing back to the humidification chamber 134. In each of the embodiments in FIGS. 19(a)-19(c), either the conduit 106 or the connector 152 has a lower region before attaching to the port 112 of the humidification chamber 134. These regions may not inhibit gas flow, but these regions may allow pooling of any condensate formed while reducing the likelihood of the condensate flowing back to the humidification chamber 134. FIG. 19(d) uses an inverted form of the previous embodiments, where a high region is located proximally with a lower more distal region following, to reduce the likelihood of any condensate from flowing back to the humidification chamber 134.

These embodiments may provide solutions for condensate formation and pooling that may occur as a result of using a horizontal connection mechanism between a humidification chamber and a conduit. It is recognised that other mechanisms to reduce the likelihood of condensate flowing back to the humidification chamber may be possible and are not excluded from the scope of the disclosed apparatus and systems.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavor in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

Where a value is used with a term of approximation, that number is intended to include the range of roundable values unless otherwise apparent from the context of use.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the present disclosure is intended to be defined only by the claims that follow.

What is claimed is:

1. A respiratory humidification system comprising:
    a humidification chamber that comprises:
        an outlet port defining at least a portion of a gases flow path, the outlet port comprising a vertical section, a horizontal section configured to engage with a connector of a conduit, and an elbow defining a transition between the vertical section and the horizontal section, the elbow defining a sharp corner, the outlet port further comprises an opening configured to receive a probe; and
        an inlet port extending vertically such that the inlet port is perpendicular to the horizontal section of the outlet port;
        a raised portion located within the horizontal section of the outlet port and adjacent to the sharp corner, the raised portion being downstream of the opening configured to receive the probe.

2. The respiratory humidification system of claim 1, wherein the raised portion inhibits liquid flowing from the conduit to the humidification chamber in use.

3. The respiratory humidification system of claim 1, wherein the raised portion fills or at least partially fills a dead space region in the gases flow path in use.

4. The respiratory humidification system of claim 1, further comprising the conduit, the conduit is configured to engage with the outlet port.

5. The respiratory humidification system of claim 1, wherein the raised portion is directly attached to the outlet port.

6. The respiratory humidification system of claim 4, wherein the conduit comprises one or more heating elements.

7. A respiratory humidification system comprising:
    a humidification chamber configured to contain a volume of liquid, the humidification chamber having:
        an outlet port comprising a horizontal section, a vertical section, and an elbow defining a transition between the horizontal section and the vertical section, the outlet port further comprising an opening configured to receive a probe; and
        an inlet port extending vertically such that the inlet port is perpendicular to the horizontal section of the outlet port;
    a conduit connectable to the outlet port of the humidification chamber, the conduit and the outlet port of the humidification chamber being connected by a connector, a gases flow path being defined from an entrance to the outlet port of the humidification chamber to an outlet of the conduit, a sharp corner positioned along the gases flow path at a location where the gases flow path makes an abrupt change in direction; and
    a raised portion located in the gases flow path directly adjacent to the sharp corner, the raised portion being downstream of the opening configured to receive the probe.

8. The respiratory humidification system of claim 7, wherein the raised portion is located immediately downstream from the sharp corner.

9. The respiratory humidification system of claim 7, wherein the raised portion is located within a region of the gases flow path that would be a recirculation region with the raised portion present.

10. The respiratory humidification system of claim 7, wherein the raised portion forms a portion of the outlet port.

11. The respiratory humidification system of claim 7, wherein the raised portion forms a portion of the connector.

12. The respiratory humidification system of claim 7, wherein the raised portion forms a portion of the conduit.

13. The respiratory humidification system of claim 7, wherein the raised portion fills at least a lower portion of at least one of a horizontal portion of the outlet port, the conduit or the connector such that condensate is less likely to flow from the conduit into the humidification chamber.

14. The respiratory humidification system of claim 13, wherein the raised portion has a tapered edge.

15. The respiratory humidification system of claim 13, wherein the raised portion has a straight edge.

* * * * *